(12) United States Patent
Maniga

(10) Patent No.: US 8,685,470 B1
(45) Date of Patent: Apr. 1, 2014

(54) NATURAL PRODUCT ENERGY FORMULATION FOR PETS AND METHOD OF USE THEREOF

(71) Applicant: Nyangenya Maniga, Gilbert, AZ (US)

(72) Inventor: Nyangenya Maniga, Gilbert, AZ (US)

( * ) Notice: Subject to any disclaimer, the term of this patent is extended or adjusted under 35 U.S.C. 154(b) by 25 days.

(21) Appl. No.: 13/850,171

(22) Filed: Mar. 25, 2013

(51) Int. Cl.
*A01N 65/00* (2009.01)

(52) U.S. Cl.
USPC ......................................................... 424/725

(58) Field of Classification Search
None
See application file for complete search history.

(56) References Cited

U.S. PATENT DOCUMENTS

2008/0305096 A1 * 12/2008 Verdegem et al. ........... 424/94.4

* cited by examiner

*Primary Examiner* — Michael Meller
(74) *Attorney, Agent, or Firm* — Kevin Hazen

(57) ABSTRACT

A natural product energy formulation is provided for a pet, which synergistically aids in (1) function of the heart, (2) energy production, such as in muscles, and/or (3) enhances removal of toxic free radicals. For example, the natural product energy formulation enhances function of the heart, by the use of $CoQ_{10}$; enables the body to produce more energy through enhanced efficiency of the Krebs cycle, such as by use of L-carnitine; and aids in the removal of waste and/or toxins produced in the body, such as by providing anti-oxidants. Hence, the energy formulation synergistically optimizes the heart, muscles, and toxin removal at the same time, which allows for a more active, healthy, and/or interactive pet, where the pet can prolong duration of exercise, increase intensity of exercise, and recover faster. The natural product formulation for pets optionally contains a lipotropic constituent to aid in fat metabolism and/or weight loss.

1 Claim, 3 Drawing Sheets

NATURAL PRODUCT ENERGY FORMULATION FOR PETS AND METHOD OF USE THEREOF

CROSS REFERENCES TO RELATED APPLICATIONS

This application is a continuation-in-part of U.S. patent application Ser. No. 13/848,625 filed Mar. 21, 2013, which is a continuation-in-part of U.S. patent application Ser. No. 13/847,414 filed Mar. 19, 2013, which claims benefit of U.S. provisional patent application No. 61/615,271 filed Mar. 24, 2012; and claims benefit of U.S. provisional patent application No. 61/623,421 filed Apr. 12, 2012, all of which are incorporated herein in their entirety by this reference thereto.

TECHNICAL FIELD OF THE INVENTION

The present invention relates to a natural product energy formulation for a pet.

DESCRIPTION OF THE RELATED ART

There exist a number of drinks designed to aid human performance. However, the human performance drinks are of three types: (1) those that provide electrolytes; (2) those that provide vitamins; and (3) those that provide energy through use of sugar and caffeine.

Examples of electrolyte providing drinks include drinks providing sodium, potassium, calcium, and magnesium. Brand name examples of electrolyte drinks include: Gatorade® (PepsiCo, Inc., Purchase, N.Y.) and Powerade® (The Coca Cola Company, Atlanta, Ga.). In the art, electrolyte providing energy drinks are used to replace electrolytes lost due to sweat.

Examples of vitamin providing drinks include drinks providing vitamin B.

Examples of energy drinks include drinks providing: caffeine and sugar. Brand name examples of energy drinks include: Red Bull® (Red Bull GmbH, Austria), Monster® (Monster Beverage Corporation, Corona, Calif.), Rockstar® (Rockstar Beverage Corporation, Lax Vegas, Nev.), and 5-Hour Energy® (Living Essentials, Wabash, Ind.). In the art, the energy drinks are used to overcome tiredness due to lack of sleep by increasing heart rate and raising sugar concentrations in the body.

PROBLEM STATEMENT

What is needed is an energy formulation that works for a pet.

SUMMARY OF THE INVENTION

The invention comprises a natural product energy formulation for a pet and method of use thereof.

BRIEF DESCRIPTION OF THE DRAWINGS

A more complete understanding of the present invention is derived by referring to the detailed description and claims when considered in connection with the Figures, wherein like reference numbers refer to similar items throughout the Figures.

Elements and steps in the figures are illustrated for simplicity and clarity and have not necessarily been rendered according to any particular sequence. For example, steps that are performed concurrently or in different order are illustrated in the figures to help improve understanding of embodiments of the present invention.

DETAILED DESCRIPTION OF THE PREFERRED EMBODIMENTS

The invention comprises a natural product formulation.

In one embodiment, one or more natural product constituents are combined with a solvent, such as water to form the natural product formulation or natural product weight loss formulation. The natural product weight loss formulation synergistically aids in (1) function of the heart, (2) energy production, such as in muscles, and/or (3) enhances removal of toxic free radicals. For example, the natural product energy formulation enhances function of the heart, by the use of $CoQ_{10}$; enables the body to produce more energy through enhanced efficiency of the citric acid cycle or Krebs cycle, such as by use of L-carnitine; and/or aids in the removal of waste and/or toxins produced in the body, such as by providing anti-oxidants. Hence, the energy formulation synergistically optimizes function of the heart, function of muscle, and toxin removal at the same time, which allows the user to prolong duration of exercise, increase intensity of exercise, and recover faster. The natural product energy formulation optionally contains no caffeine or sugar while retaining efficacy.

In another embodiment, the natural product formulation is prepared in a form suitable for a pet.

In yet another embodiment, the natural product formulation is supplemented with one or more lipotropic constituents, which results in a natural product nutrition/weight loss formulation.

In still yet another embodiment, the natural product formulation is supplemented with one or more vitamins, amino acids, and/or electrolytes, which results in a natural product nutrition formulation.

In yet still another embodiment, the natural product formulation is supplemented with a form of caffeine and/or a form of sugar, which results in a natural product/stimulation energy formulation.

In another embodiment, the natural product energy formulation is supplemented with at least two of and preferably all of: (1) one or more vitamins, amino acids, and/or electrolytes; (2) a form of caffeine and/or a form of sugar; and (3) at least one lipotropic constituent, which results in a supplemented natural product formulation.

Energy Formulations

Figure 1:
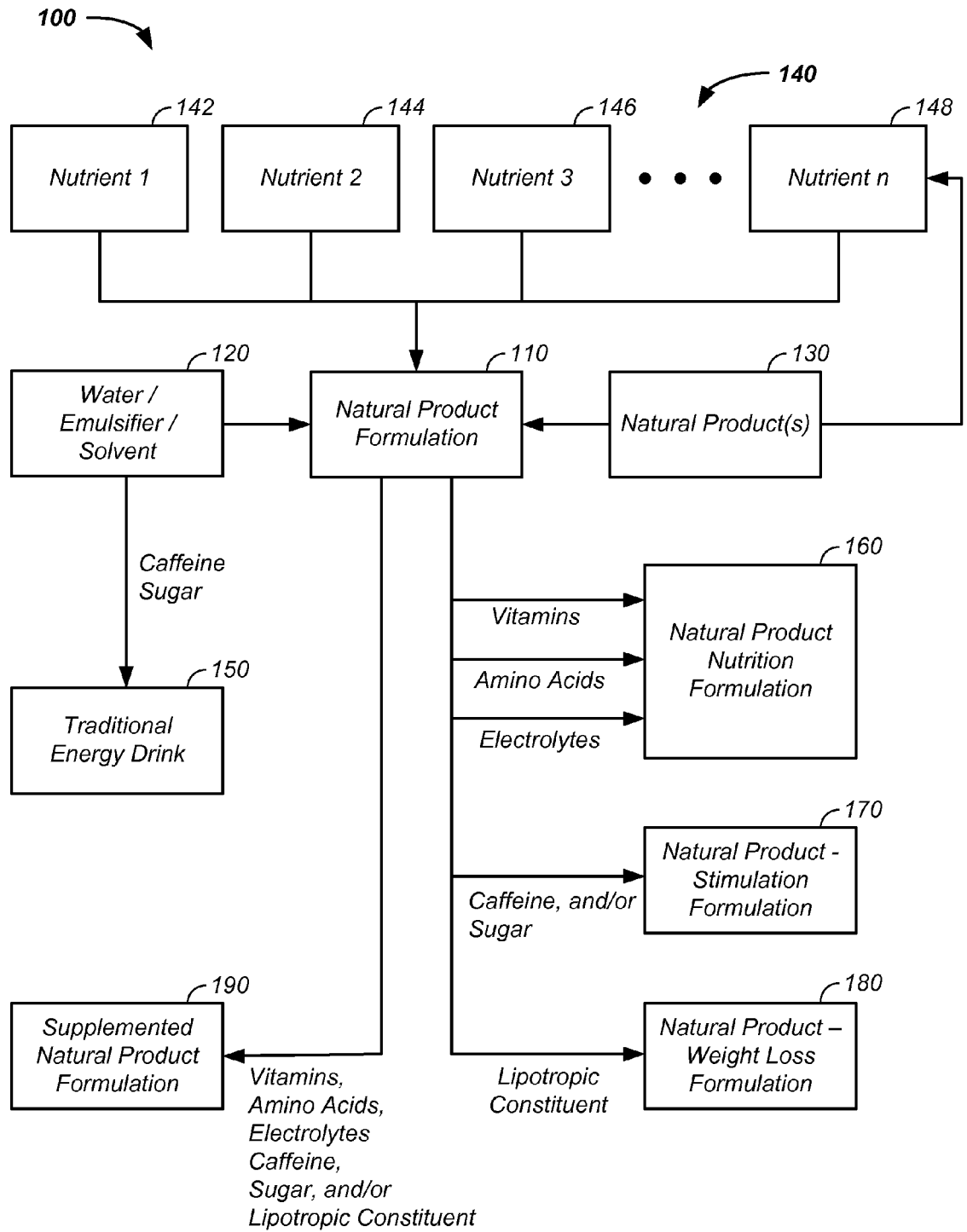
FIG. 1 illustrates a natural product formulation.

Referring now to FIG. 1, a flow chart illustrating formation of an energy formulation 100 is provided. FIG. 1 contrasts a traditional energy drink 150 with a natural product energy formulation 110, each of which are further described infra.

Still referring to FIG. 1, a traditional energy drink 150 is a solution of a solvent 120, such as water, mixed with caffeine and/or sugar.

Still referring to FIG. 1, herein a natural product energy formulation 110 is a combination of a solvent 120, a natural product 130, and/or a nutrient 140. The solvent 120 is any liquid, aqueous mix, non-aqueous based solvent, water, an emulsifier, and/or a suspension agent. Herein, a natural product 130 is a chemical, chemical compound, or substance produced by a living organism found in nature. The natural product 130 is produced by a plant or animal.

Herein, a nutrient 140 is a product derived from a natural product, is a constituent of a natural product, or is a simulant of a constituent of a natural product. For example, pine bark is a natural product produced by the maritime pine tree (*Pinus pinaster*). An extraction of the natural product 130 of pine bark is pine bark extract, which is a nutrient 140. An example of the extracted constituent is a chemical from the class of extracted naturally occurring chemicals referred to as proanthocyanidins. An artificially produced chemical simulant of a natural product nutrient is a chemical, substance, and/or mixture that retains one or more properties of the nutrient 140, but is man-made. The natural product formulation 110 optionally contain 1, 2, 3, . . . n nutrients 142, 144, 146, 148, where n is a positive integer. Herein, sugar and caffeine are not in the class of natural products 130.

In stark contrast to a traditional energy drink 150, which contains high concentrations of sugar and/or caffeine, the nutrition energy formulation 110 contains no caffeine, no sugar, a low concentration of sugar, a low concentration of caffeine, or a high concentration of sugar with a low concentration of caffeine. Herein, a high concentration of caffeine is the caffeine in a cup of coffee or more and a high concentration of sugar is the concentration of sugar in a traditional non-diet soda. For example, traditional brewed coffee has about 80 to 135 mg of caffeine per serving, which is about 386 to 652 mg of caffeine per liter and traditional coca cola contains 34 mg or caffeine per serving or 96 mg of caffeine per liter. Traditional energy drinks 150 contain higher amounts of caffeine per serving and higher concentrations of caffeine. For example, Red Bull® contains 80 mg or caffeine per serving and 320 mg of caffeine per liter. In stark contrast, the nutrition energy formulation preferably contains no caffeine per serving and optionally contains less than 1, 2, 4, 8, 10, 15, 20, or 25 mg of caffeine per serving or less than 5, 10, 20, 40, 60, or 80 mg of caffeine per liter. The sugar is optionally present in the natural product stimulation formulation at a level of at least 1, 2, 3, 4, 5, 10, 15, 20, or 30 grams per serving.

Still referring to FIG. 1, a natural product energy formulation 110 is optionally combined with: (1) vitamins to form a vitamin enhanced natural product formulation, (2) amino acids to form an amino acid enhanced natural product formulation or protein enhanced natural product formulation, or (3) electrolytes to form an electrolyte enhanced natural product formulation. Generally, the natural product formulation 110 is optionally supplemented with vitamins, amino acids (such as L-leucine), electrolytes, and/or an additive to form a natural product nutrition formulation 160.

Still referring to FIG. 1, a natural product energy formulation 110 is optionally combined with: caffeine and/or sugar to form a natural product/stimulation formulation 170.

Still referring to FIG. 1, a natural product energy formulation 110 is optionally combined with a form of a lipotropic constituent, such as: a choline; a betaine; an inositol; L-carnitine or any constituent containing the base of L-carnitine, such as acetyl carnitine; malic acid or a form thereof, such as magnesium malate or a synthetic simulant; and/or methionine to form a natural product weight loss formulation 180. For example, carnitine or a quaternary ammonium compound is used to transport fatty acids from the cytosol into the mitochondria during the breakdown of lipids or fats for the generation of metabolic energy. More specifically, carnitine transports long-chain acyl groups from fatty acids into a mitochondrial matrix, where the fat is broken down through n-oxidation to the molecule of Acetyl coenzyme A or acetyl CoA, which is a molecule input into the Krebs cycle.

Still referring to FIG. 1, a natural product energy formulation 110 is optionally combined with any of: (1) vitamins, amino acids, and/or electrolytes; (2) caffeine and/or sugar; and (3) at least one lipotropic constituent to form a supplemented natural product formulation 190.

In still yet another embodiment, the supplemented natural product formulation includes one of more of a form of: a methylxanthine, caffeine, a B vitamin, an herb, carbonated water, guarana, yerba mate, açai, taurine, ginseng, maltodextrin, inositol, carnitine, creatine, glucuronolactone, ginkgo biloba, sugar, a choline, a betaine, a methionine, artificial sugar, and L-carnitine.

In still another embodiment, the natural product formulation 110 is a solid, powder, mixture, or emulsion containing no solvent or less than 1, 2, 3, 5, 10, or 15 percent water and/or a solvent.

Natural Products

Generally, a natural product is a chemical compound or substance produced by a living organism. A natural product can be considered as such even if it can be prepared by total synthesis. Herein, natural products used in the natural product formulation 110 include energy ingredients, lipotropic ingredients, and/or anti-oxidant ingredients.

Examples of energy inducing natural products used in the natural product formulation 110 include, but are not limited to, a form of: ginseng, French pine bark, grape seed, pine bark, and a Stevia herb or shrub. Examples of a nutrient 140 is an extract, laboratory produced product, or simulant of a constituent or extract of any natural product. Examples of a nutrient include, but are not limited to: a betaine, a carnitine, a choline, a form of coenzyme $Q_{10}$, an inositol, L-carnitine, a pyruvate, a taurine, and/or an extract, such as a ginseng extract, a grape seed extract, a pine bark extract, and/or a Stevia extract. Herein, amino acids, caffeine, sugar, and vitamins are preferably not included in the basic natural product formulation 110; however, they are optionally included in a supplemented form of the natural product energy formulation, as described supra.

Examples of an anti-oxidant used in the natural product formulation include, but are not limited to: a super anti-oxidant, a form of alpha lipoic acid, an extract of Noni, pomegranate, a resveratrol, and/or tea, such as a green tea, or an extract of Noni, pomegranate, and/or tea.

The concentration of any of the natural product 130, nutrients 140, or additives in the natural product formulation 110 or a derivative thereof is in the range of zero to ten percent and more preferably in the range of 0.001 to 10 percent, and still more preferably some of the constituents are in the range of 2 to 5 percent. Similarly, the concentration of any of the natural product 130, nutrients 140, or additives in the natural product formulation 110 or a derivative thereof is in the range of zero to 1000 mg/dose and more preferably in the range of zero to ten mg/dose and still more preferably in the range of 0.001 to 10 mg/dose, and yet still more preferably some of the constituents are in the range of 2 to 5 mg/dose.

In one example, the natural product formulation and/or natural product weight loss formulation includes the constituents of:

an energy production component, comprising:
        a citric acid cycle usable form of L-carnitine;
    a heart function component, comprising:
        a form of coenzyme $Q_{10}$; and
    a toxin removal component, comprising:
        a resveratrol, where co-delivery of all of: the energy production component, the heart function component, and the toxin removal component synergistically enhances efficiency of the energy production component in the heart through removal of citric acid cycle localized toxins by the toxin removal component. Optionally and preferably, for each dose, each constituent of the natural product weight loss formulation includes greater than one-thousandth of a gram and less than five grams. Further, the inventor has determined that certain ratios of the energy production component to the heart function component and/or the toxin removal component are more synergistic. For examine, the ratio of the energy production component is preferably at least a 1:1 mass-to-mass ratio relative to either the heart function component or to the toxin removal component and optionally is a ratio of less than 2:1, 3:1, 4:1, 5:1, or 6:1 mass-to-mass. Less optimally, the ratio of the energy production component to either the heart function component of the toxin removal component is less than 1:2 or 1:3, mass-to-mass. Similarly, the inventor has determined that certain mass-to-mass ratios of the heart function component relative to the toxin removal component yield superior gains in the energy production unit and/or overall feeling of stamina/recovery, such as less than 1:3, 1:2, 1:1, 2:1, or 3:1. In yet another example, the composition includes L-carnitine as high as 250 to 1500 mg/day, $CoQ_{10}$ as high as 30 to 200 mg/day and resveratrol as high as 100 to 200 mg/day.

Function

A traditional energy drink 150 uses caffeine, which is a stimulant, and/or sugar. The effect of the traditional energy drink 150 is merely to pump more blood, which supplies more oxygen. However, if the body is depleted of nutrition, the traditional energy drink 150 has no effect. In stark contrast, the natural product energy formulation 110 provides nutrients to the blood or body through ingestion, inhalation, adsorption, or through a skin or body membrane. For example, the natural product energy formulation 110 enhances function of the heart, by the use of $CoQ_{10}$. Further, the natural product energy formulation 110 enables the body to produce energy through enhanced efficiency of the Krebs cycle, through enhanced production of energy in muscles, and through the increased use of fat as a fuel, such as by use of L-carnitine. Hence, the energy formulation synergistically optimizes the heart and muscles at the same time. Still further, the natural product energy formulation 110 aids in the removal of waste and/or toxins produced in the body, such as by providing anti-oxidants. As a result, in one example the natural product energy formulation 110 aids in function of the heart and muscles at the same time, which enhances the ability to exercise, while simultaneously aiding in the removal of toxic free radicals, such as those produced in exercise, from the body.

For example, the body makes its energy at the cellular level (mitochondria) through the tricarboxylic acid cycle, citric acid cycle, or Krebs cycle. Ingredients in the natural product energy formulation include those that the body uses in its metabolism of energy derived from the Krebs cycle. They work to synergistically balance use of B vitamins and super-antioxidants, such as coenzyme $Q_{10}$ and L-carnitine. At the same time, the natural product energy formulation or drink increases the release of energy from food efficiently, such as by enabling the body to convert fats and carbohydrates into energy. For example, the natural product formulation 110 is combined with at least one lipotropic constituent to form the natural product weight loss formulation 180. Ultimately the result is abundant energy and less fatigue and more muscle with less fat.

In various forms, the natural product energy formulation 110 aids in metabolism, fat burning, and/or in providing cellular energy.

Metabolism

In another example, the natural product energy formulation 110 is composed of at least three important nutrient groups for a healthy metabolism, liver, and heart. These ingredient groups are:
 a lipotropic ingredient for the efficient transfer of fats and toxins from the liver;
 a vitamin B complex and/or amino acids necessary for efficient metabolism of fats and carbohydrates into energy; and
 a super anti-oxidant, which protects the liver and body tissues from damage from free radicals, which ensures healthy liver, blood vessels, and heart, and which further contributes to low levels of LDL cholesterol, homocysteine, and triglycerides, all of which contribute to heart disease at high concentration.

The combination of these ingredients helps to increase fat burning into energy leading to a lean body, healthy blood vessels, and/or a healthy heart.

Fat Removal and Burning

In another example, the natural product energy formulation 110 contains lipotropic ingredients, which aid the liver by dissolving, removing, and/or burning off fats for energy. The lipotropic ingredients also prevent fat deposition onto the liver. These events lead to low levels of fat deposition in the body and hence loss of weight. Optional lipotropic ingredients in the natural product energy formulation 110 include, but are not limited to, one or more of:
 betaine, also called trimethyl glycine (TMG), which is a methyl donor for tissue repair and which reduces homocysteine levels;
 inositol, which reduces fat infiltration of the liver by the dissolution, transfer, and metabolism of liver fat;
 L-methionine, which detoxifies and helps to regenerate live cells, repairs and reverses damaged liver cells, helps to lower cholesterol, and protects against a fatty liver;
 choline, which helps transport fat from the liver, is a methyl donor and precursor to acetylcholine, and is necessary for liver regeneration and overall health, herein choline is used to describe a class of various quaternary ammonium salts containing the N,N,N-trimethyl-ethanolammonium cation, such as in lecithin;
 L-carnitine and/or simulant or derivative thereof; and
 a form of malic acid, such as magnesium malate.

Cellular Energy

In yet another example, the natural product energy formulation 110 aids in production of energy at the cellular level through the Krebs cycle. For instance, the natural product energy formulation 110 ingredients include a vitamin $B_{12}$, B12, and/or a B12 lipotropic complex that the body uses in its metabolism of energy derived from the Krebs cycle, which increases the release of energy from food efficiently, enables the body to convert fats and carbohydrates into energy, and ultimately results in abundant energy, less fatigue, more muscle, and less fat.

Benefits

The inventor has determined and observed benefits of the natural product energy formulation 110, which include: ability to exercise for longer duration, ability to exercise with increased intensity, reduced recovery time, a decrease in cholesterol concentration, a decrease in blood pressure, an enhanced ability to sleep, an increased mental alertness, and/or an increased sexual drive. Simply, it improves the overall health of the body. Taken early in the morning, during the day, and/or before exercise, the body's endurance and resistance to fatigue is increased.

Form

The natural product energy formulation 110 is optionally used in a number of forms. For clarity, the description herein is provide for the natural product energy formulation 110 in a solution that is ready to drink, from a small container, in a dilute form from a larger container, or as a teaspoon dose. However, the natural product energy formulation 110 is optionally provided in alternative forms. First, the natural product energy formulation 110 is optionally provided as a concentrate, allowing the user to mix with water or into a food or beverage. The concentrate is at least 2, 3, 4, 5, 10, 15, or 20 times the concentration of the above described ready to drink formulation. Second, the natural product energy formulation 110 is optionally provided in the form of a sublingual spray and/or a sublingual drop. Third, the natural product energy formulation 110 is optionally provided in powder form, which is mixed by the user as needed into a solution, is added directly to a food substrate, or is directly ingested. Fourth, the natural product energy formulation 110 is optionally provided in a patch, such as a dermal or transdermal patch, which delivers the formulation or a subset thereof into the skin or through the skin, respectively.

Figure 2:
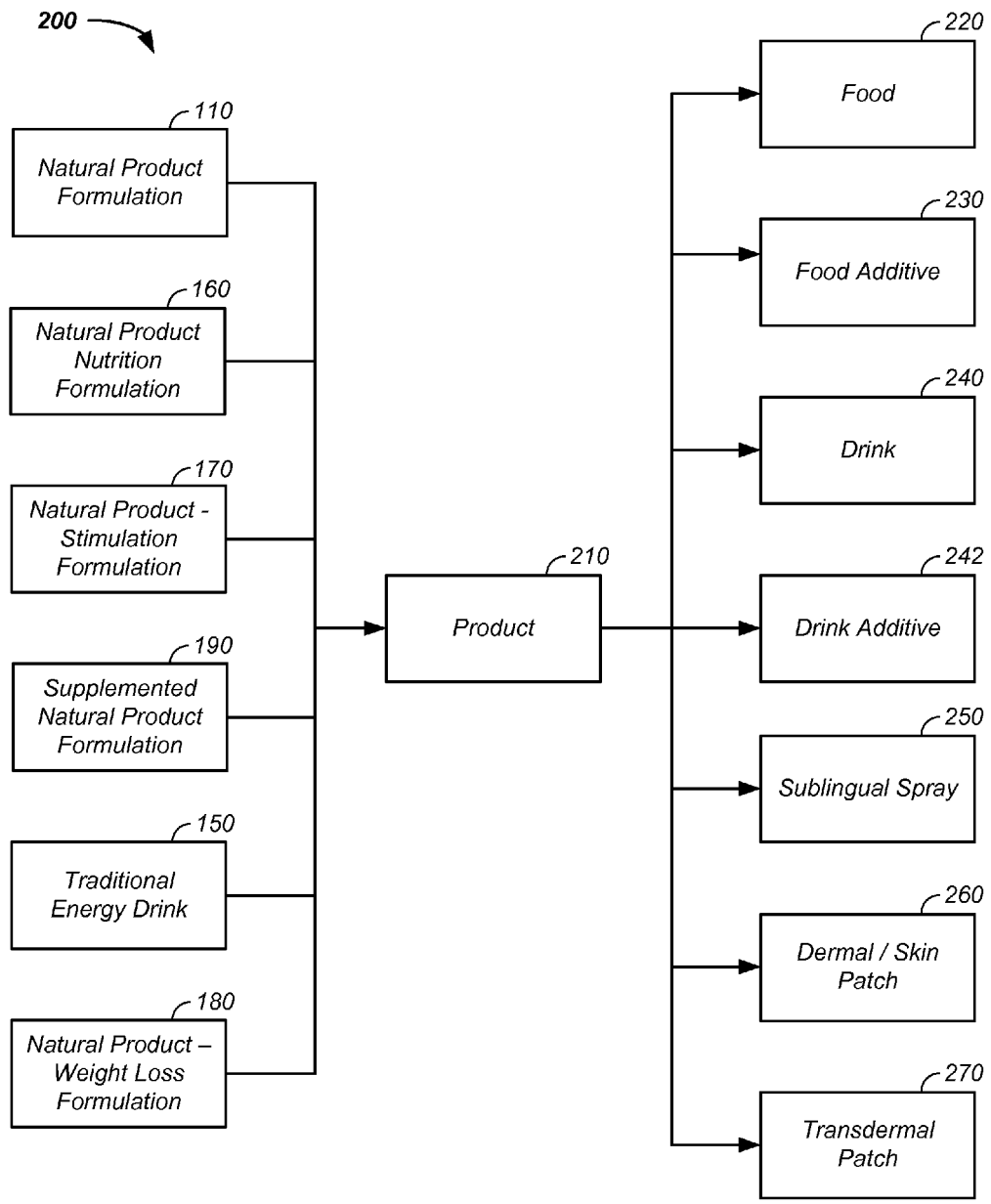
FIG. 2 illustrates use of a natural product formulation.

Referring now to FIG. 2, use of the natural product 200 is illustrated. A product 210 is made using at least one of:
- the natural product formulation 110;
- the natural product nutrition formulation 160;
- the natural product stimulation formulation 170;
- the natural product weight loss formulation 180;
- the supplemented natural production formulation 190; and/or
- a form, simulant, and/or extract of at least two of: betaine; a trimethyl glycine; inositol; L-methionine; choline; Lecithin; malic acid, such as magnesium malate; ginseng; French pine bark; grape seed; pine bark; a Stevia herb or shrub, carnitine, a form of coenzyme $Q_{10}$, an inositol, L-carnitine, a pyruvate, a taurine, a ginseng extract, a grape seed extract, a pine bark extract, a Stevia extract, a super anti-oxidant, a form of alpha lipoic acid, an extract of Noni, pomegranate, a resveratrol, and/or tea, such as green tea.

The product 210 is incorporated into food 220, used as a food additive 230, incorporated into or used directly as a drink 240, is used as a drink additive 242, used in a sublingual spray 250, provided as an aerosol or mist for inhalation, used in a dermal skin patch 260, and/or is used in a transdermal patch 270.

Generally, the formulation and/or the natural product formulation is contained in any container, in any form, and optionally includes any label directing use. The form is optionally a dry powder, a dry mixture, a liquid, or a wet food, such as a canned moist pet food or pet supplement.

Spray Bottle

Optionally, the formulation is maintained in a liquid form deliverable via a spray bottle, such as a sublingual spray delivery bottle. In one example, the spray bottle contains a manual pump, a pressurized pump, and/or a pressurized/compressed canned air propulsion fluid delivery system. For clarity of presentation, a manual pump spray bottle is further described herein without loss of generality. The pump is attached to a tube, such as a plastic tube, that draws a liquid form of the formulation from a bottom of a reservoir in the spray bottle container. The pump forces the liquid formulation down a narrow barrel and out a small hole at a muzzle of the spray bottle. The hole, nozzle, and/or aperture serves to focus the flowing liquid into an accelerated stream suitable for sublingual spray delivery. The pump optionally includes a piston housed inside a cylinder, typically with a small spring. To operate the pump, the pump is depressed pushing the piston into the cylinder. The moving piston compresses the spring, so when you release the trigger, the piston is pushed back out of the cylinder. These two strokes of the piston, into the cylinder and out again, constitute the entire pump cycle. For example, in the downstroke, the piston pushes in, shrinks the area of the cylinder, and forces fluid out of the pump and in the upstroke the spring pushes the piston back out, expands the cylinder area, and sucks fluid into the pump. In the sublingual spray bottle, the pump only forces the fluid up in one direction and not back into the reservoir using a one-way valve. Optionally, the spray bottle has two one-way valves in the pumping system: one between the pump and the reservoir and one between the pump and the nozzle. Typically, the valve between the pump and the reservoir includes a tiny rubber ball that rests inside a small seal. The sides of the seal are optionally angled so that the ball won't fall through. Depending on the design, either gravity or a small spring holds this ball against the seal so that the water passageway is blocked off when the operator is not pumping. When the piston moves out, such as when an operator releases the trigger or pump, the expanding area of the cylinder sucks on the fluid below, pulling the ball up out of the seal. Since the ball is lifted up, fluid is free to flow from the reservoir. However, when the operator squeezes the pump, the outward force of the moving fluid pushes the ball into the seal, blocking off the passageway to the reservoir. Consequently, the pressurized fluid is pushed only into the barrel and subsequently out of the spray nozzle.

Liquid Dropper Bottle

In yet another embodiment, the formulation is contained in a bottle as a fluid, where the bottle contains a liquid dropper tube, such as a sublingual liquid dropper delivery tube tapered at one end with a bulb for forcing air/fluid movement relative to the tube on the opposite end. The liquid dropper is suitable for delivery of the liquid formulation under the tongue of an individual and/or a pet.

Dermal/Skin Patch

A dermal patch or skin patch is a medicated adhesive patch that is placed on the skin to deliver a medication into the skin. This is in contrast to a transdermal patch, which delivers the medication through the skin and into the bloodstream. Herein, a weight loss skin patch is an adhesive patch that contains a weight loss formulation delivered into the skin when placed onto the skin.

Transdermal Patch

A traditional transdermal patch is a medicated adhesive patch. Herein, a weight loss transdermal patch is an adhesive patch that is placed on the skin or scales of a fish to deliver a specific dose of a formulation through the skin and into the bloodstream. An advantage of a transdermal formulation delivery route over other types of formulation delivery, such as oral, topical, intravenous, and intramuscular is that the patch provides a controlled release of the formulation into the patient, subject, or pet, through a porous membrane covering a reservoir of the formulation and/or through body heat melting thin layers of a formulation support matrix embedded in the adhesive. The formulation is optionally a natural product formulation, weight loss formulation, energy formulation, medication formulation, or any combination thereof.

Pet Formulation

In another embodiment, any of the natural product formulations described herein are provided in a form suitable for a pet. Herein, a pet is an animal other than a human, such as a cat, dog, rodent, mammal, and fish.

Figure 3:
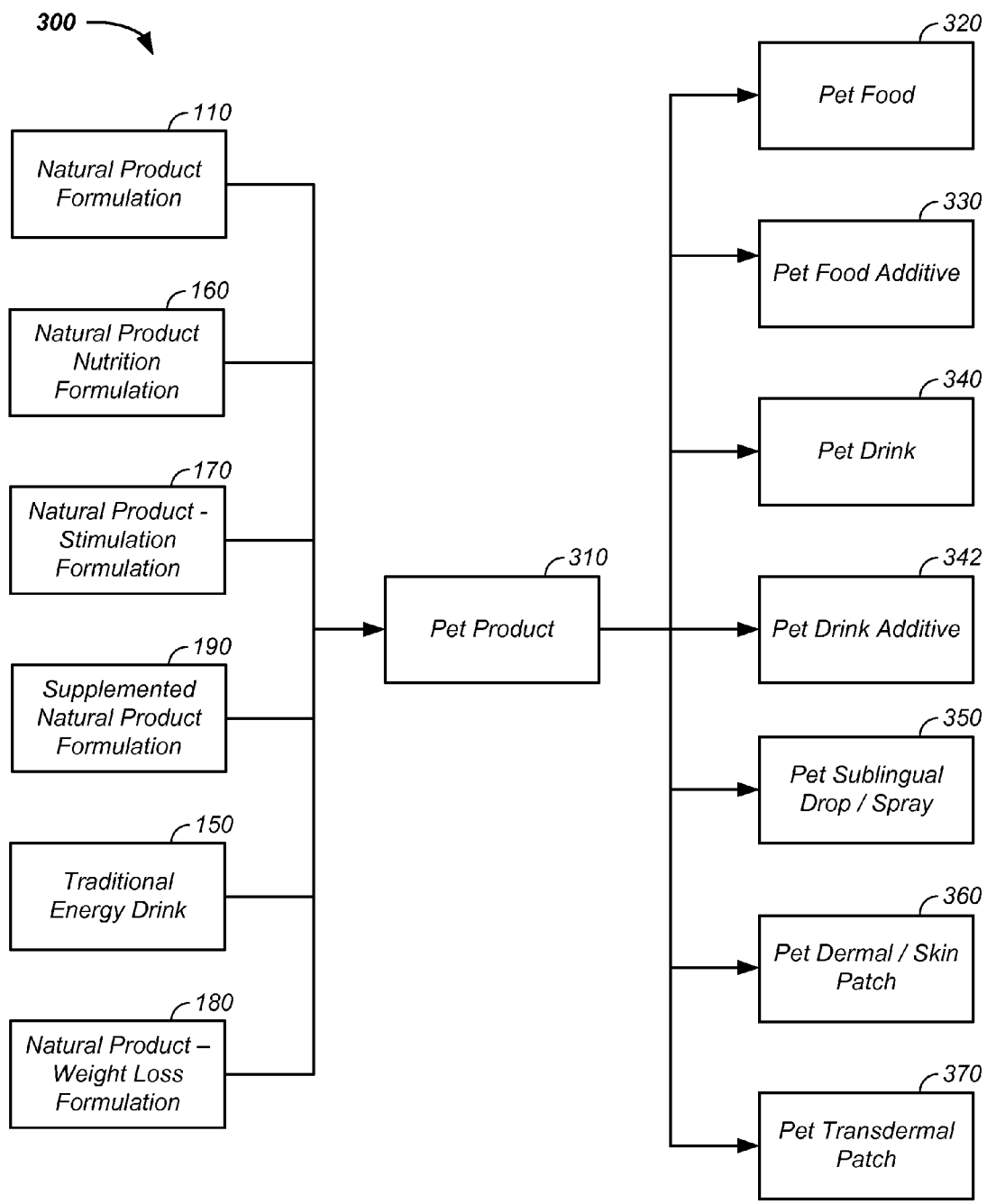
FIG. 3 illustrates use of a natural product formulation for a pet.

Referring now to FIG. 3, use of the natural product with pets 300 is illustrated. A pet product 310 is made using at least one of:
- a traditional energy drink 150;
- the natural product formulation 110;
- the natural product nutrition formulation 160;
- the natural product stimulation formulation 170;
- the natural product weight loss formulation 180;
- the supplemented natural production formulation 190; and/or
- a form, simulant, and/or extract of at least two of: betaine; a trimethyl glycine; inositol; L-methionine; choline; Lecithin; malic acid, such as magnesium malate; ginseng; French pine bark; grape seed; pine bark; a Stevia herb or shrub, carnitine, a form of coenzyme $Q_{10}$, an inositol, L-carnitine, a pyruvate, a taurine, a ginseng extract, a grape seed extract, a pine bark extract, a Stevia extract, a super anti-oxidant, a form of alpha lipoic acid, an extract of Noni, pomegranate, a resveratrol, and/or tea, such as green tea.

The pet product 310 is incorporated into a pet supplement and/or a pet food 320, used as a pet food additive 330, incorporated into or used directly as a pet drink 340, is used as a pet drink additive 342, used in a pet sublingual drop and/or spray 350, provided as an aerosol or mist for inhalation, used in a pet dermal skin patch 360 or scale patch, and/or is used in a pet transdermal patch 370.

Still yet another embodiment includes any combination and/or permutation of any of the energy formulation and/or nutrition formulation constituents described herein.

The particular implementations shown and described are illustrative of the invention and its best mode and are not intended to otherwise limit the scope of the present invention in any way. Indeed, for the sake of brevity, conventional manufacturing, connection, preparation, and other functional aspects of the system may not be described in detail. Furthermore, the connecting lines shown in the various figures are intended to represent exemplary functional relationships and/ or physical couplings between the various elements. Many alternative or additional functional relationships or physical connections may be present in a practical system.

In the foregoing description, the invention has been described with reference to specific exemplary embodiments; however, it will be appreciated that various modifications and changes may be made without departing from the scope of the present invention as set forth herein. The description and figures are to be regarded in an illustrative manner, rather than a restrictive one and all such modifications are intended to be included within the scope of the present invention. Accordingly, the scope of the invention should be determined by the generic embodiments described herein and their legal equivalents rather than by merely the specific examples described above. For example, the steps recited in any method or process embodiment may be executed in any order and are not limited to the explicit order presented in the specific examples. Additionally, the components and/or elements recited in any apparatus embodiment may be assembled or otherwise operationally configured in a variety of permutations to produce substantially the same result as the present invention and are accordingly not limited to the specific configuration recited in the specific examples.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present invention, in addition to those not specifically recited, may be varied or otherwise particularly adapted to specific environments, manufacturing specifications, design parameters or other operating requirements without departing from the general principles of the same.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

The invention claimed is:

1. A composition for increased sexual drive consisting essentially of therapeutically effective amounts of yerba mate extract, pomegranate extract, gingko extract and acai extract.

* * * * *